(12) United States Patent  
Mettler, Jr.

(10) Patent No.: US 9,808,227 B2  
(45) Date of Patent: Nov. 7, 2017

(54) TONGUE RETRACTION AND CLEANING METHOD AND APPARATUS

(75) Inventor: Gilbert William Mettler, Jr., Washington, NH (US)

(73) Assignee: Q-In Medical Technologies, LLC, Buffalo, WY (US)

(*) Notice: Subject to any disclaimer, the term of this patent is extended or adjusted under 35 U.S.C. 154(b) by 900 days.

(21) Appl. No.: 12/013,911

(22) Filed: Jan. 14, 2008

(65) Prior Publication Data

US 2009/0182364 A1 Jul. 16, 2009

(51) Int. Cl.

| A61B 1/32 | (2006.01) |
|---|---|
| A61B 13/00 | (2006.01) |
| A01K 13/00 | (2006.01) |
| A61B 17/24 | (2006.01) |
| A61D 15/00 | (2006.01) |
| A61B 1/24 | (2006.01) |

(52) U.S. Cl.
CPC ............ *A61B 13/00* (2013.01); *A01K 13/001* (2013.01); *A61B 17/244* (2013.01); *A61D 15/00* (2013.01); *A61B 1/24* (2013.01)

(58) Field of Classification Search
CPC ....................................................... A61B 13/00
USPC .......................................... 606/161; 600/240
See application file for complete search history.

(56) References Cited

U.S. PATENT DOCUMENTS

| 118,386 A | 8/1871 | Osborn |
|---|---|---|
| 412,409 A | 10/1889 | Osborne |
| 477,791 A | 6/1892 | Andrews |
| 883,106 A | 3/1908 | Galloway |
| 1,042,133 A | 10/1912 | Marshall |
| 2,218,072 A | 10/1940 | Runnels |
| 2,491,274 A | 12/1949 | McNeill |
| 2,543,999 A | 3/1951 | Voss |
| 2,583,750 A * | 1/1952 | Runnels ................. 606/161 |
| 2,653,597 A | 9/1953 | Canan |

(Continued)

FOREIGN PATENT DOCUMENTS

| EP | 1034721 A1 | 9/2000 |
|---|---|---|
| EP | 2240070 B1 | 11/2013 |

(Continued)

OTHER PUBLICATIONS

US 8,622,898, 01/2014, Mettler, Jr. (withdrawn)

(Continued)

*Primary Examiner* — Gregory Anderson  
*Assistant Examiner* — Sarah Simpson  
(74) *Attorney, Agent, or Firm* — Schwegman Lundberg & Woessner, P.A.

(57) ABSTRACT

One embodiment includes an apparatus for retracting an animal tongue that includes a handle that is elongate and that includes a proximal portion and a distal portion and a tongue receiving cup coupled to the distal portion of the handle, the tongue receiving cup being generally concave and sized such that a first side of the tongue receiving cup extends over a first side of the tongue, a second side opposite the first side extends over a second side of the tongue that is opposite the first side of the tongue, a dorsal portion of the cup extends along the dorsal portion of the tongue and a posterior extending tip extends at least partially along the back of the tongue, the first side, second side, and posterior extending tip defining a tongue receiving cavity of the tongue receiving cup.

21 Claims, 8 Drawing Sheets

(56) References Cited

U.S. PATENT DOCUMENTS

| | | | |
|---|---|---|---|
| 2,723,661 A | 11/1955 | Hull | |
| 3,768,477 A | 10/1973 | Anders et al. | |
| 3,863,627 A | 2/1975 | Bouffard | |
| 3,890,960 A | 6/1975 | Wunsch | |
| 3,943,592 A | 3/1976 | Bhaskar et al. | |
| 1,187,079 A | 6/1976 | Miller | |
| D243,422 S | 2/1977 | Varga | |
| 4,079,478 A | 3/1978 | Andrews | |
| D263,743 S | 4/1982 | Priestman | |
| 4,455,704 A * | 6/1984 | Williams | 15/111 |
| 4,589,848 A | 5/1986 | Inoue | |
| 4,638,521 A | 1/1987 | Potente et al. | |
| D305,797 S | 1/1990 | Robinson et al. | |
| D309,528 S | 7/1990 | Valenti | |
| D317,821 S | 6/1991 | Aoyagi | |
| 5,176,151 A | 1/1993 | Harding | |
| 5,226,197 A | 7/1993 | Nack et al. | |
| D344,335 S | 2/1994 | Elisha | |
| D359,556 S | 6/1995 | Hale et al. | |
| 5,518,503 A | 5/1996 | Rooney et al. | |
| 5,553,627 A | 9/1996 | Newkirk | |
| 5,656,014 A | 8/1997 | Rooney et al. | |
| D391,370 S | 2/1998 | Cho | |
| 5,730,597 A | 3/1998 | Luttrell | |
| 5,735,864 A | 4/1998 | Heisinger, Jr. | |
| 5,774,925 A | 7/1998 | Pryor, III et al. | |
| 5,779,654 A | 7/1998 | Foley et al. | |
| 5,810,856 A | 9/1998 | Tveras | |
| 5,817,114 A | 10/1998 | Anderson et al. | |
| D406,891 S | 3/1999 | Smith | |
| 5,893,860 A | 4/1999 | Ripich et al. | |
| 5,897,492 A | 4/1999 | Feller et al. | |
| 5,910,151 A | 6/1999 | Adedokun | |
| 5,984,935 A * | 11/1999 | Welt et al. | 606/161 |
| 6,015,293 A * | 1/2000 | Rimkus | 433/141 |
| 6,045,499 A | 4/2000 | Pitesky | |
| 6,083,235 A | 7/2000 | Wagner | |
| D433,134 S | 10/2000 | Pitesky | |
| 6,142,777 A | 11/2000 | Winston et al. | |
| 6,352,545 B1 | 3/2002 | Wagner | |
| 6,440,149 B1 | 8/2002 | Potti | |
| 6,520,953 B1 | 2/2003 | Schultz | |
| D471,276 S | 3/2003 | Potti | |
| 6,655,960 B2 | 12/2003 | Fischer | |
| D484,978 S | 1/2004 | Syal | |
| D502,263 S | 2/2005 | Feller et al. | |
| 6,921,409 B2 | 7/2005 | Richard | |
| D523,299 S | 6/2006 | Johnson | |
| D536,452 S | 2/2007 | Geiberger et al. | |
| D545,445 S | 6/2007 | Klein | |
| D574,494 S | 8/2008 | Schmitt | |
| D594,122 S | 6/2009 | Mettler | |
| 8,740,788 B1 | 6/2014 | Mettler, Jr. | |
| 2002/0128673 A1 | 9/2002 | Ripich et al. | |
| 2004/0152031 A1 * | 8/2004 | Takahashi | 433/1 |
| 2006/0025791 A1 | 2/2006 | Ripich et al. | |
| 2006/0036133 A1 * | 2/2006 | Demsky | 600/240 |
| 2007/0163064 A1 * | 7/2007 | Wong et al. | 15/143.1 |
| 2008/0045988 A1 * | 2/2008 | Abbott et al. | 606/161 |
| 2008/0154291 A1 * | 6/2008 | Bosma et al. | 606/161 |
| 2008/0208228 A1 * | 8/2008 | Mueller | 606/161 |
| 2009/0111069 A1 | 4/2009 | Wagner | |

FOREIGN PATENT DOCUMENTS

| | | |
|---|---|---|
| WO | WO-2009091529 A2 | 7/2009 |
| WO | WO-2009091529 A3 | 7/2009 |

OTHER PUBLICATIONS

"U.S. Appl. No. 29/302,281, Non-Final Office Action dated Sep. 16, 2008", 11 pgs.

"U.S. Appl. No. 29/302,281, Notice of Allowance dated Jan. 28, 2009", 6 pgs.

"U.S. Appl. No. 29/302,281, Response filed Dec. 15, 2008 to Non-Final Office Action dated Sep. 16, 2008", 7 pgs.

"International Application Serial No. PCT/US2009/000198, Search Report dated Jul. 27, 2009", 4 pgs.

"International Application Serial No. PCT/US2009/000198, Written Opinion dated Jul. 27, 2009", 4 pgs.

"U.S. Appl. No. 12/794,686, Notice of Allowance dated Jan. 21, 2014", 7 pgs.

"U.S. Appl. No. 12/794,686, Examiner Interview Summary dated Jul. 12, 2013", 4 pgs.

"U.S. Appl. No. 12/794,686, Notice of Allowance dated Aug. 29, 2013", 10 pgs.

"U.S. Appl. No. 12/794,686, Pre-Interview Communication dated Jan. 15, 2013", 3 pgs.

"U.S. Appl. No. 12/794,686, Response filed Dec. 4, 2012 to Restriction Requirement dated Sep. 28, 2012", 7 pgs.

"U.S. Appl. No. 12/794,686, Restriction Requirement dated Sep. 28, 2012", 7 pgs.

"European Application Serial No. 09702805.4, Response filed Feb. 14, 2013 to Extended European Search Report dated Jul. 27, 2012", 14 pgs.

"European Application Serial No. 09702805.4, Supplementary European Search Report dated Jul. 27, 2012", 7 pgs.

"International Application Serial No. PCT/US2009/000198, International Preliminary Report on Patentability dated Jul. 20, 2010", 6 pgs.

Glazer, H. S., "What's Hot and What's Getting Hotter", *ACD Impact*, (Sep. 2012), 20-21.

* cited by examiner

TONGUE RETRACTION AND CLEANING METHOD AND APPARATUS

TECHNICAL FIELD

Various embodiments described herein relate generally to oral tools, including a tongue retraction and cleaning method and apparatus.

BACKGROUND

Care providers need to manage the location of the tongue during examination and treatment of patients. Additionally, care providers need to clean tongues. Patients could, in some cases, provide these services for themselves. Accordingly, apparatus, system and method are needed to provide these benefits, among others.

DETAILED DESCRIPTION

Figure 1:
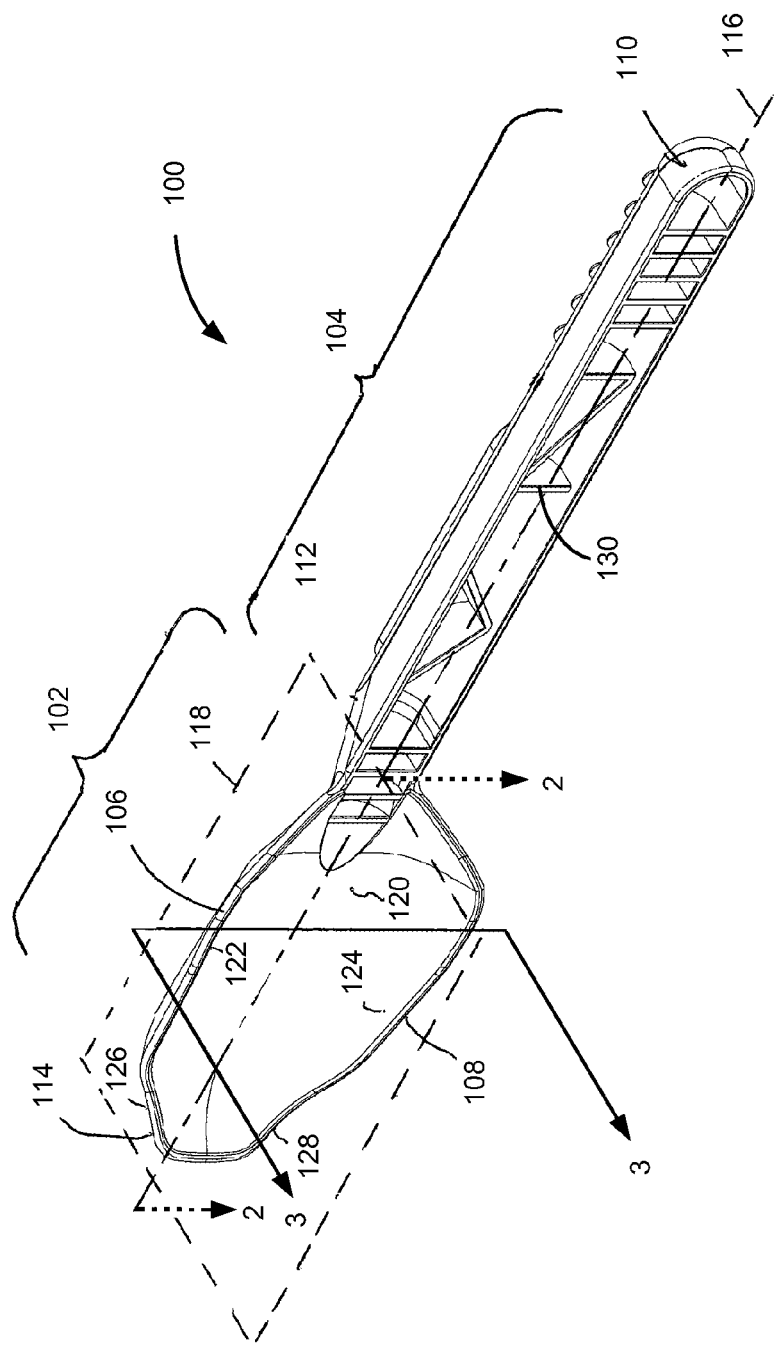
FIG. 1 illustrates a perspective view of a tongue retractor, according to one embodiment.
Figure 2:
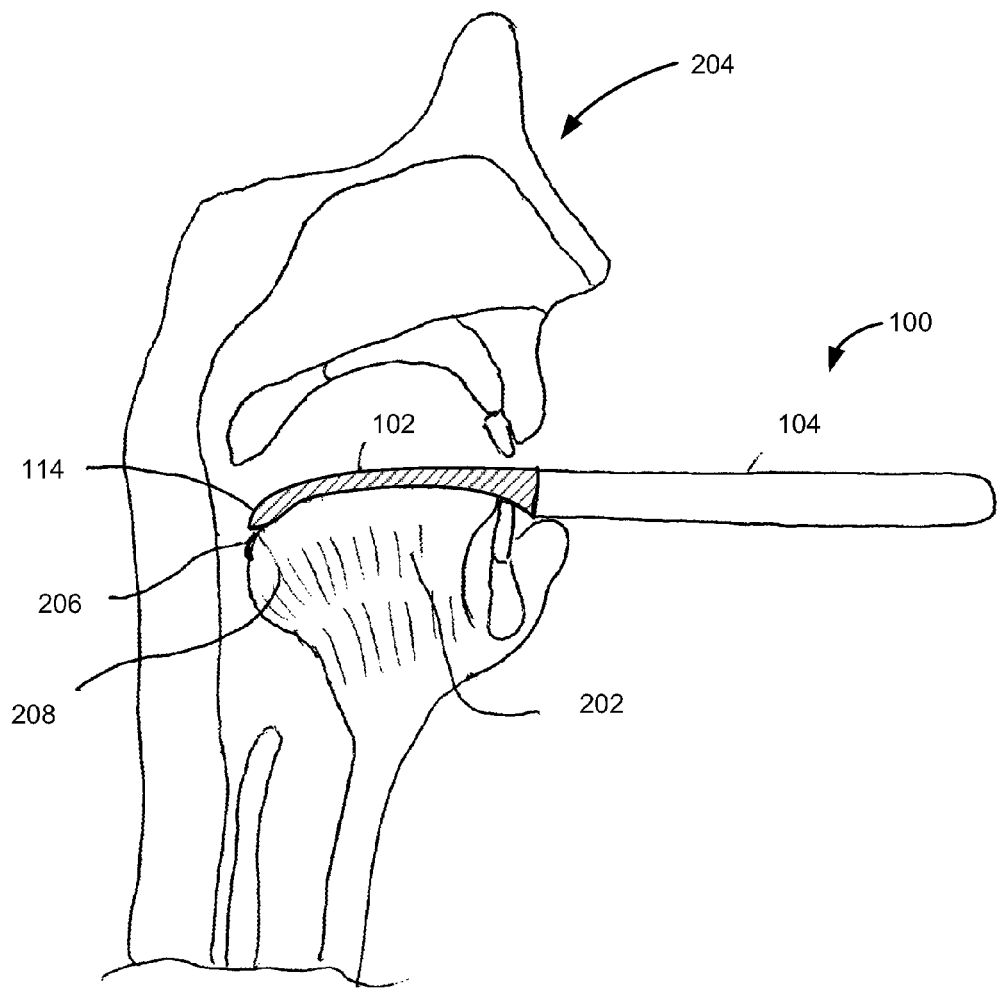
FIG. 2 illustrates a human and a partial cross section of a tongue retractor taken along line 2-2 in FIG. 1.

FIGS. 1-4 illustrate a tongue retractor 100 according to some embodiments, and the tongue retractor in use. Although these figures are directed toward a tongue retractor, embodiments that additionally clean the tongue are contemplated, as disclosed herein. In various embodiments, the tongue retractor 100 includes a tongue receiving cup 102 for cupping and retracting a tongue via force applied using the handle 104. The tongue receiving cup 102 is coupled to the handle 104. Various coupling means are possible, including, but not limited to, molding, welding, adhesive, and the like. In some examples, a cup and the handle are part of a continuous mold. A partial cross section of the tongue retractor 100 as applied to the tongue 202 of an animal 204 is illustrated in FIG. 2, according to one embodiment.

The present subject matter is effective on animals. Animals contemplated include, but are not limited to, humans, canines and felines. The present subject matter is for use by various care providers, including medical doctors and associated care providers, dentists and associated care providers and veterinary doctors and associated care providers. Consumers additionally are able to purchase devices disclosed herein over the shelf and apply them to one or more animals such as humans or other animals. Dental procedures contemplated include, but are not limited to, titanium spray, computer aid design rendering, computer aided machining, surgery and tooth reconstruction, as well as various hygienist procedures.

In various embodiments, the devices disclosed herein are sized for use on a particular animal. For example, in some embodiments, the present subject matter is sized for use with humans. In additional embodiments, the present subject matter is sized for use with other animals. Embodiments that are sized for use on multiple animals are additionally contemplated. Further, embodiments that are sized for an animal at a particular stage of growth (e.g., an infant stage, an adult stage, etc.) are contemplated.

The embodiments disclosed herein include several size variables that are sized to fit a particular animal. FIG. 2 illustrates a human and a partial cross section of a tongue retractor taken along line 2-2 in FIG. 1. The tongue retractor 100 provides a means for cupping the tongue. Means for cupping the tongue comprise any of the devices described herein that contact at least a dorsal portion of the tongue. In some embodiments, the tongue retractor 100 provides a means for cupping the tongue without extending over circumvallate papillae of the tongue 202 when the tongue receiving cup 102 is mated to the tongue. In additional embodiments, the tongue receiving cup 102 extends over the circumvallate papillae. The example illustrated in FIG. 2 demonstrates a tongue retractor 100 that includes a tongue receiving cup 102 cross sectioned at an anterior posterior dorsal ventral plane, also known as a sagittal plane, and that has a form factor that substantially matches a cross section of the tongue 202 cross sectioned at the anterior posterior dorsal ventral plane. In some embodiments, the form factor does not extend around the tip of the tongue. Embodiments which extend around the tip of the tongue, such as by extending between the tongue 202 and one or more teeth such as incisors of the animal, are contemplated.

Figure 3:
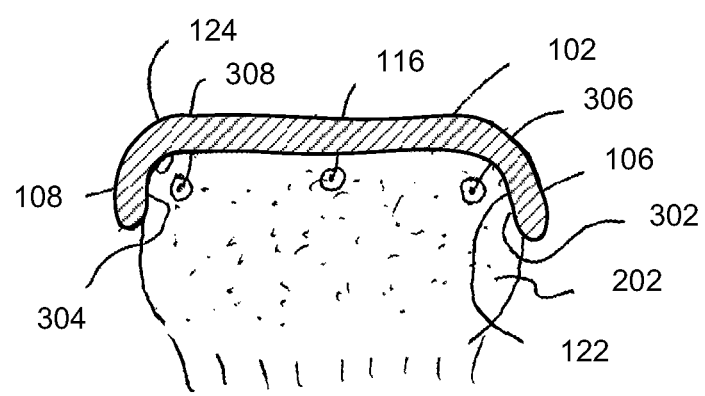
FIG. 3 illustrates a human and a partial cross section of a tongue retractor taken along line 3-3 in FIG. 1.

FIG. 3 illustrates a human and a partial cross section of a tongue retractor taken along line 3-3 in FIG. 1. Although a tongue retractor is disclosed in the illustration, embodiments that additionally adapted to clean the tongue are contemplated, as disclosed herein. In the illustration, the tongue retractor 100 defines a cross section of the tongue receiving cup 102 at a left right dorsal ventral plane, also known as a coronal plane, that has a form factor that substantially matches a cross section of the tongue 202 at the left right dorsal ventral plane of the animal to which the tongue retractor 100 is being applied to.

Returning to the embodiment of FIG. 1, the handle 104 is elongate comprising a proximal portion 110 and a distal portion 112. The handle 104 includes at least one reinforcement 130 to resist shape deformation of the handle 104. The tongue retractor includes a tongue receiving cup 102 coupled to the distal portion 112 of the handle 104. In various embodiments, the tongue receiving cup 102 is generally concave. In the embodiment illustrated in FIG. 3, the tongue receiving cup 102 is sized such that a first side 106 of the tongue receiving cup 102 extends at least partially over a first lateral side 302 of the tongue 202. The tongue receiving cup 102 illustrated additionally extends at least at least partially over a second lateral side 304 of the tongue 202 that is opposite the first lateral side 302 of the tongue 202. The tongue receiving cup 102 additionally extends over a dorsal portion of the tongue. In some embodiments this includes only the oral portion of the tongue. In additional embodiments, this includes the back of the tongue, also referred to as the oral pharyngeal portion of the tongue. As illustrated in FIG. 2, the tongue receiving cup 102 includes a tip 114 that extends at least partially along the back 208 of the tongue 202 toward and along the oral pharyngeal portion of the tongue. In various embodiments, the first side 106, second side 108, and the tip 114 define a tongue receiving cavity of the tongue receiving cup 102.

The perspective view of FIG. 1 illustrates a major axis 116. A proximal portion 110 is located at a first end of the major axis 116 and the distal portion 112 is located opposite the proximal portion in a distal direction along the major axis 116. The tongue receiving cup 102 is coupled to the handle 104 at the distal portion 112 of the handle. In various embodiments, the tongue receiving cup 102 is bisected by a major plane 118 along the major axis 116. The tongue receiving cup 102 is one of several shapes contemplated, and other shapes, including irregular shapes, are possible without departing from the present subject matter.

Figure 4:
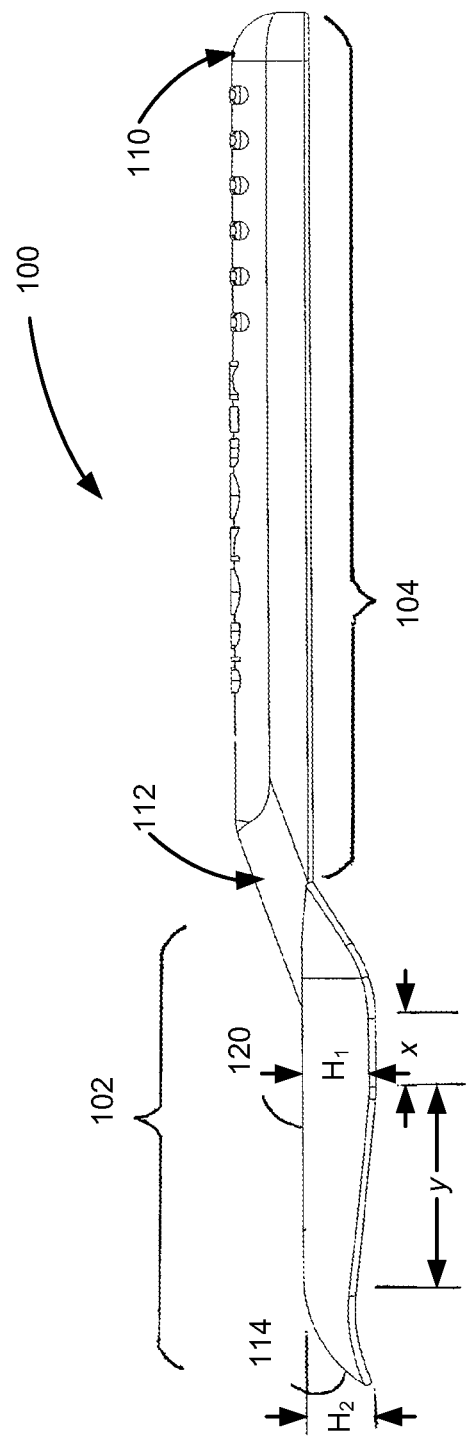
FIG. 4 illustrates a side view of a tongue retractor, according to one embodiment.

In various embodiments, the tongue receiving cup 102 includes a base 120 that is generally planar, with the base being perpendicular to the major plane 118. The base 120 is at least partially disposed along a dorsal surface of the tongue in various embodiments. The first side 106 of the tongue receiving cup 102 includes a first wall 122 curving away from the base 120 in a direction away from the major plane 118, the first wall 122 curving around a first wall axis 306, illustrated in FIG. 3, that is parallel to the major axis 116. A second wall 124 opposite the first wall 122 is illustrated, with the second wall curving away from the base 120 in a direction away from the major plane 118, the second wall curving around a second wall axis 308 opposite the first wall axis 306 with respect to the major axis 116, the second wall axis 308 being parallel to the major axis 116, wherein the first wall 122 and the second wall 124 define a first cup portion x, as illustrated in FIG. 4, that has a first regular height $H_1$ measured from the base 120. FIG. 4 illustrates a side view of a tongue retractor, according to one embodiment. A second cup portion y has a gradually declining height measured from the base 120 in the distal direction.

In various embodiments, the tip 114 is bisected by the major plane 118. The tip 114, in some instances, curves away from the base 120 in a direction distal from the handle, the tip having a height $H_2$ measured from the base that is greater than the height of the second cup portion, and lesser than the height $H_1$ of the first cup portion. Embodiments in which the height $H_2$ is greater than the height $H_1$ are additionally contemplated. A first webbing 126 curving away from the base 120 and joins the first wall 122 and the tip 114, in some embodiments. In additional embodiments, a second webbing 128 curves away from the base 120 and joins the second wall 124 and the tip 114. In various embodiments, the base 120, first wall 122, the second wall 124, the tip 114, the first webbing 126 and the second webbing 128 define a concave cavity, with the junction between the base 120, the first wall 122, the second wall 124, the tip 114, the first webbing 126 and the second webbing 128 being curved.

The present subject matter comprises various materials, including, but not limited to, biocompatible embodiments of ultra high molecular weight polyethylene ("UHMWPE"), ultra low molecular weight polyethylene ("ULMWPE-PE-WAX"), high molecular weight polyethylene (HMWPE), high density polyethylene ("HDPE"), high density cross-linked polyethylene ("HDXLPE"), cross-linked polyethylene ("PEX"), medium density polyethylene ("MDPE"), low density polyethylene ("LDPE"), linear low density polyethylene ("LLDPE"), very low density polyethylene ("VLDPE"), polyamide such as Nylon®, polypropylene, polyvinylchloride, polystyrene including, but not limited to, high density polystyrene, polylactic acid, cellulose based products including, but not limited to wood, other plant based materials including starches such as carbohydrates, and biocompatible metal alloys such as stainless steel. Combinations of these and other materials are possible. Some embodiments mold a plastic handle to a stainless steel cup, and vice versa. Various embodiments are opaque. Additional embodiments are transparent or semi-transparent. Embodiments including tint are contemplated. Embodiments in which a cup is tinted one color, while a handle is tinted another color are contemplated. Various textures are contemplated including, but not limited to, gloss texture, matte texture, and other textures.

Figure 5:
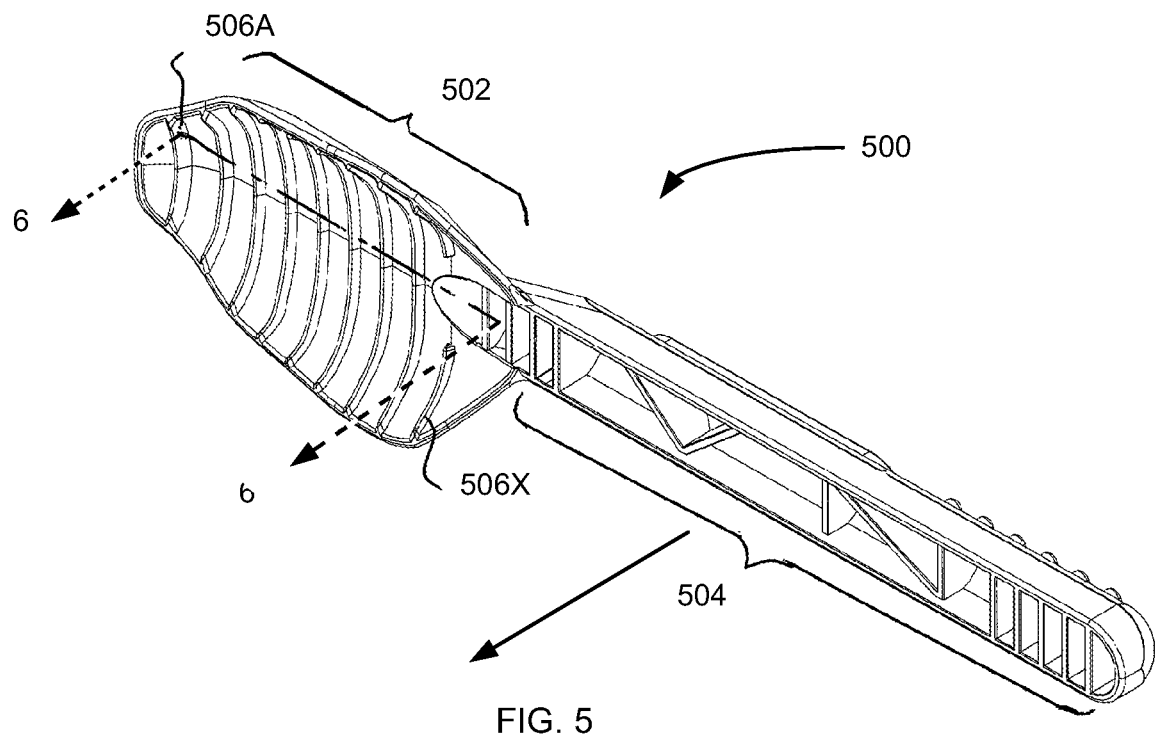
FIG. 5 illustrates a perspective view of a tongue retractor and cleaner, according to one embodiment.

FIG. 5 illustrates a perspective view of a tongue retractor and cleaner 500, according to one embodiment. The illustrated embodiment is for retracting at least a portion of the lateral sides of an animal tongue, at least a portion of the back of the animal tongue, and a dorsal portion of an animal tongue and for cleaning the animal tongue. The tongue retractor includes a cup 502 and a handle 504. The tongue retractor and cleaner additionally include means for cleaning the tongue coupled to the means for cupping the tongue. Cleaning means comprise any of the structures described herein that interrupt the continuity of the inner, concave side of the tongue cupping structures described herein. For example, the plurality of cleaning elements 506A-506X are coupled to the tongue receiving cup 102 extending away from the tongue receiving cup 102 and into the tongue receiving cavity. Embodiments that include a single cleaning element are contemplated.

Figure 6:
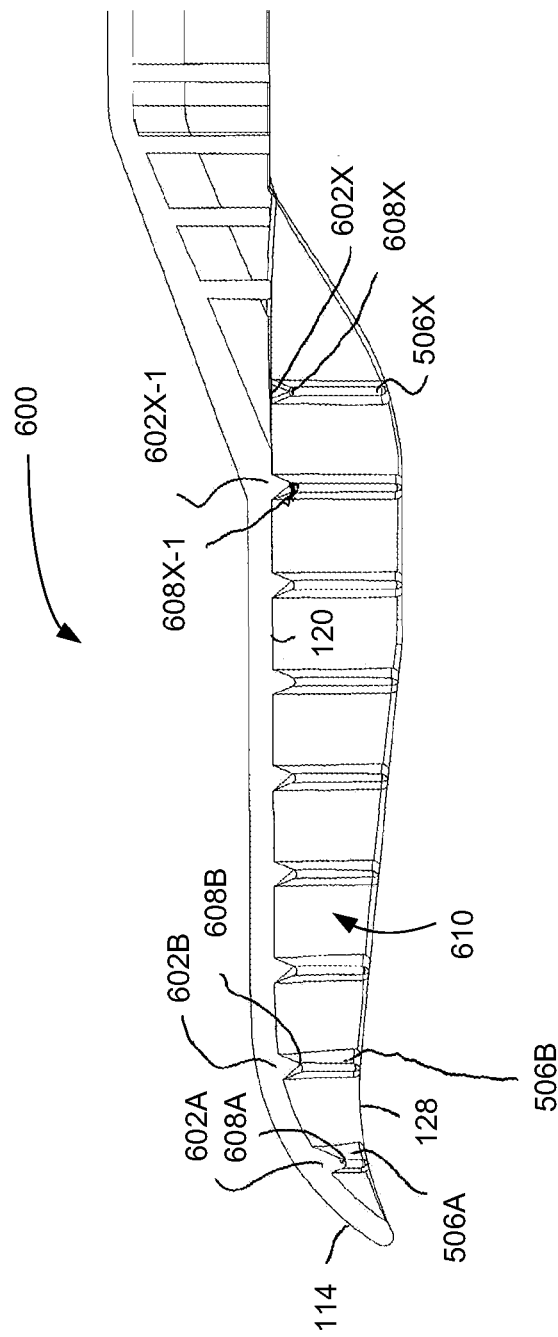
FIG. 6 illustrates a partial cross section of a tongue retractor and cleaner taken along line 6-6 in FIG. 5.

Various cleaning element shapes are contemplated. FIG. 6 illustrates a partial cross section of a tongue retractor and cleaner taken along line 6-6 in FIG. 5. FIG. 6 illustrates a tongue retracting and cleaning tool 600 including a plurality of cleaning elements 506A-506X, each having a generally triangular cross section, with a base 602A-602X of each triangular cross section coupled to the base of the cup 604 such than an apex 608A-608X of each triangle is disposed inside the concave cavity 610. In some examples, the cleaning elements have a triangular cross section along a cross section along an anterior posterior dorsal ventral plane, also known as a sagittal plane. In some instances, each triangular cross section of the plurality of cleaning elements defines respective isosceles triangles. Other embodiments define triangles having other shapes, including triangles that define an acute angle with respect to a base of a cup.

With reference to FIG. 4, the height of the cleaning elements crossing the base, the height measured from the base 120, is less than the height H1. This height is additionally less than the height of the second section in some examples. Further, this height is less than the height H2 in some examples. In various examples, the plurality of cleaning elements 506A-506X each are generally linear along a respective cleaning element axis, with each respective cleaning element axis being generally perpendicular to the major axis 116 as referred to in FIG. 1 of the handle 104. In additional examples, the cleaning elements have a semi-circular cross section along an anterior posterior dorsal ventral plane, also known as a sagittal plane, with the base of each cleaning element coupled to the tongue receiving cup 102. Some examples include cleaning elements that have a triangular cross section along the major plane 118. Some examples include plurality of cleaning elements coupled to the tip that are disposed in the tongue receiving cavity. In various examples, the plurality of cleaning elements each extend along the first wall, the second wall, and the base. Some of these examples include cleaning elements that additional extend along the tip.

Figure 7:
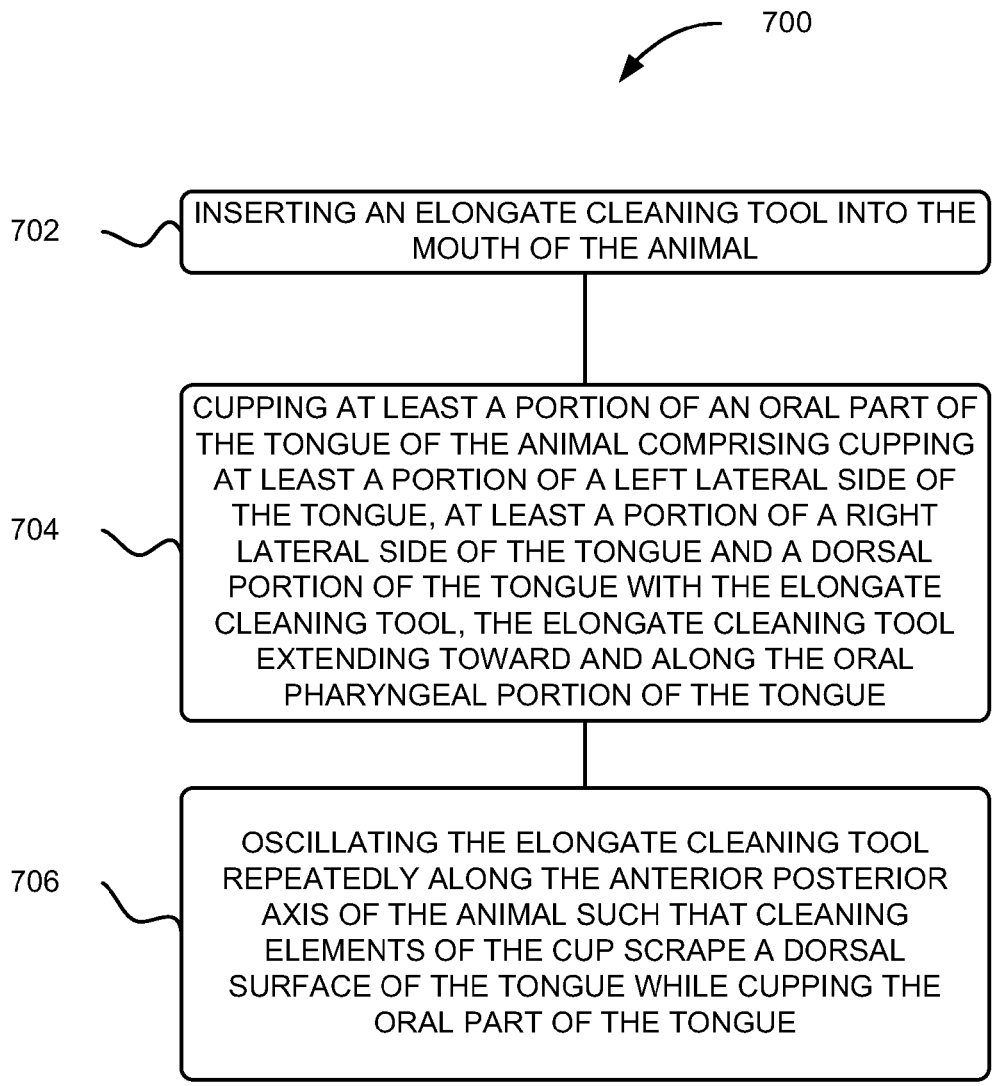
FIG. 7 illustrates a method of cleaning a tongue, according to one embodiment.

FIG. 7 illustrates a method 700 of cleaning a tongue, according to one embodiment. At 702, a method for cleaning an animal tongue includes inserting an elongate cleaning tool into the mouth of the animal. At 704, the method includes cupping at least a portion of an oral part of the tongue of the animal comprising cupping at least a portion of a left lateral side of the tongue, at least a portion of a right lateral side of the tongue and a dorsal portion of the tongue with the elongate cleaning tool, the elongate cleaning tool extending toward and along the oral pharyngeal portion of the tongue. At 706, the method includes oscillating the elongate cleaning tool repeatedly along the anterior posterior axis of the animal such that cleaning elements of the cup scrape a dorsal surface of the tongue while cupping the oral part of the tongue. Some methods include oscillating the elongate cleaning tool repeatedly along the anterior posterior axis of the animal such that the cleaning elements of the cup scrape the left lateral side of the tongue and the right lateral side of the tongue. Some methods include cupping the tongue of the animal with the elongate cleaning tool to reduce the potentiating of a pharyngeal ("gag") reflex. Optional methods include oscillating the elongate cleaning and retracting element without provoking a pharyngeal ("gag") reflex.

Figure 8:
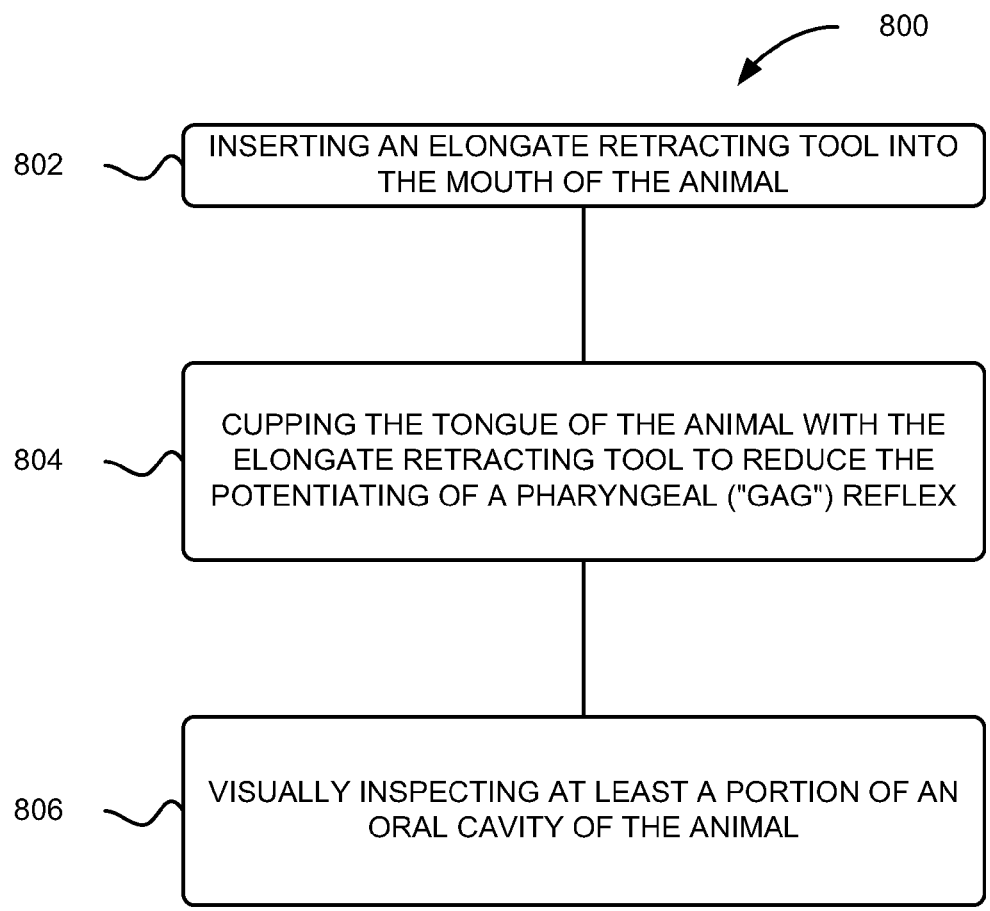
FIG. 8 illustrates a method of retracting a tongue, according to one embodiment.

FIG. 8 illustrates a method 800 of retracting a tongue, according to one embodiment. One method includes, at 802, inserting an elongate retracting tool into the mouth of the animal. At 804, the method includes cupping the tongue of the animal with the elongate retracting tool to reduce the potentiating of a pharyngeal ("gag") reflex. At 806, the method includes visually inspecting at least a portion of an oral cavity of the animal. Some methods include performing a dental procedure on the animal.

Some methods include cupping the tongue such that the tongue is substantially depressed in a ventral direction of the animal. Additional methods include cupping the tongue such that the tongue is substantially depressed in a lateral direction of the animal.

Various methods of manufacture are contemplated, including injection molding the elongate cleaning and retracting tool. Some methods include modeling the animal tongue and rapid prototyping the elongate cleaning and retracting tool such that the cup form fits the tongue. Some embodiments disposed herein position a parting line such that the parting line is out of contact with tissue of the patient. For example, in some embodiments, the parting line is on a ventral surface of a tongue receiving cup, rather than being on the sides.

One or more of the devices and methods demonstrated herein are useful for dorsal and lateral retraction of the tongue. Additionally, the present subject matter is useful for anterior and posterior retraction of the tongue. The present subject matter demonstrated here demonstrates several benefits, such as dorsal and lateral tongue retraction to expose various dental areas for oral procedures. Oral procedures include, but are not limited to, removal of foreign debris, dental examinations, surgeries, hygienist examinations, suturing, dental restoration, endodontic procedures, oral cancer screening examinations and any related intra-oral dental procedure. During one or more of these procedures, the present subject matter reduces the potentiating of a pharyngeal ("gag") reflex. The present subject matter disclosed herein can be used during collection of oral and throat culture specimens. In additional embodiments, it can be used during upper or hard palette procedures. Embodiments of the present subject matter can be used to retract oral cheek areas while performing oral procedures. For example, some embodiments enhance suctioning during oral procedures by providing for greater exposure of areas needed to be suctioned.

In some instances, the present subject matter is additionally useful for tongue cleaning and scraping to improve oral hygiene. Such embodiments can reduce halitosis. Some embodiments help reduce bacterial buildup on tongue surface. Embodiments disclosed herein provide for tongue scraping while reducing the potentiating of a pharyngeal ("gag") reflex. The present subject matter provides increased scraping and cleaning area by providing a plurality of cleaning elements, as disclosed herein.

It will be readily understood to those skilled in the art that various other changes in the details, material, and arrangements of the parts and method stages which have been described and illustrated in order to explain the nature of this invention may be made without departing from the principles and scope of the invention as expressed in the subjoined claims.

It is emphasized that the Abstract is provided to comply with 37 C.F.R. §1.72(b) requiring an Abstract that will allow the reader to quickly ascertain the nature and gist of the technical disclosure. It is submitted with the understanding that it will not be used to interpret or limit the scope or meaning of the claims.

What is claimed is:

1. An apparatus for retracting at least a portion of sides of an animal tongue, at least a portion of a back of the animal tongue, and a dorsal portion of an animal tongue, comprising:
   a tongue retraction handle that is elongate comprising a proximal portion that extends along a reference plane toward a distal portion, with the tongue retraction handle generally disposed above the reference plane; and
   a tongue retraction cup coupled the distal portion of the tongue retraction handle, the tongue retraction cup extending along the reference plane and generally beneath the reference plane, the tongue retraction cup being generally concave and sized to locate a first side of the tongue retraction cup over a first lateral side of the tongue to forcibly retract the tongue laterally, the tongue retraction cup being sized to locate a second side opposite the first side and over a second side of the tongue that is opposite the first lateral side of the tongue to forcibly retract the tongue laterally, the tongue retraction cup being sized to locate a dorsal portion of the cup along the dorsal portion of the tongue and a posterior extending tip at least partially along the back of the tongue toward an oral pharyngeal portion of the tongue to retract the tongue, the first side, second side, and posterior extending tip defining a tongue receiving cavity of the tongue retraction cup,
   wherein the tongue retraction cup is sized to locate the first side over the first side of the tongue while the second side is disposed over the second side of the tongue, and the dorsal portion of the cup is disposed over the back of the tongue, and
   wherein the apparatus is formed of one or more materials adapted to maintain a shape, including an orientation of the tongue retraction handle with respect to the tongue retraction cup, to forcibly retract the animal tongue laterally.

2. The apparatus of claim 1, wherein the apparatus is for cleaning the animal tongue, and further comprising cleaning elements coupled to the tongue retraction cup and extending away from the tongue retraction cup and into the tongue receiving cavity.

3. The apparatus of claim 1, wherein a cross section of the cup at a left right dorsal ventral plane has a form factor that substantially matches a cross section of the tongue at a left right dorsal ventral plane.

4. The apparatus of claim 1, wherein a cross section of the cup at an anterior posterior dorsal ventral plane has a form factor that substantially matches a cross section of the tongue at the anterior posterior dorsal ventral plane.

5. The apparatus of claim 1, wherein the tongue retraction cup comprises polyethylene.

6. The apparatus of claim 5, wherein the tongue retraction cup comprises high density polyethylene.

7. The apparatus of claim 1, wherein the tongue retraction cup comprises polyamide.

8. The apparatus of claim 1, wherein the tongue retraction cup comprises polypropylene.

9. The apparatus of claim 1, wherein the tongue retraction cup comprises stainless steel.

10. The apparatus of claim 1, wherein the tongue retraction cup comprises cellulose.

11. The apparatus of claim 1, wherein the animal is a human.

12. An apparatus for retracting an animal tongue, comprising:
   a tongue retraction handle that is elongate along a major axis extending through a reference plane and comprises a proximal portion at a first end of the major axis and a distal portion opposite the proximal portion in a distal direction along the major axis, with the tongue retraction handle generally disposed above the reference plane;
   a cup coupled to and continuous with the tongue retraction handle at the distal portion of the tongue retraction handle, the cup extending along the reference plane and generally beneath the reference plane, the cup bisected by a major plane perpendicular to the reference plane along the major axis, the cup generally symmetrical across the major plane, the cup comprising:
      a base that is generally planar with a base being perpendicular to the major plane;
      a first wall curving away from the base in a direction away from the major plane, the first wall curving along a first wall axis that is parallel to the major axis, wherein the cup is sized to locate the first wall of the cup over a first lateral side of the tongue to forcibly retract the tongue laterally;
      a second wall opposite the first wall, the second wall curving away from the base in a direction away from the major plane, the second wall curving along a second wall axis that is parallel to the major axis, wherein the cup is sized to locate the second wall of the cup over a second lateral side of the tongue to forcibly retract the tongue laterally, wherein the first wall and the second wall define a first cup portion that has a first regular height measured from the base, and a second cup portion that has a gradually declining height measured from the base in the distal direction;
      a tip bisected by the major plane and curving away from the base in a direction distal from the tongue retraction handle, a back wall having a height measured from the base that is greater than the height of the second cup portion, and lesser than the height of the first cup portion, wherein the cup is sized to locate the tip of the cup over a back side of the tongue to forcibly retract the tongue;
      a first webbing curving away from the base and joining the first wall and the back wall; and
      a second webbing curving away from the base and joining the second wall and the back wall,
      wherein the base, first wall, the second wall, the tip, the first webbing and the second webbing define a concave cavity, with a junction between the base, the first wall, the second wall, the tip, the first webbing and the second webbing being curved,
   wherein the cup is sized to locate the first wall over a first side of the tongue while the second side is disposed over a second side of the tongue, and
   wherein the apparatus is formed of one or more materials adapted to maintain a shape, including an orientation of the tongue retraction handle with respect to the cup, to forcibly retract the animal tongue laterally.

13. The apparatus of claim 12, further comprising a plurality of cleaning elements, each having a generally triangular cross section, with a base of each triangular cross section coupled to the base of the cup such than an apex of each triangle is disposed inside the concave cavity at a height measured from the base that is less than the first cup portion, the second cup portion, and the tip, the plurality of cleaning elements each being generally linear along a respective cleaning element axis, with each respective cleaning element axis being generally perpendicular to the major axis of the tongue retraction handle.

14. The apparatus of claim 13, wherein cleaning elements have a semi-circular cross section along a cross section, with a planar base of each cleaning element coupled to the cup.

15. The apparatus of claim 13, wherein the plurality of cleaning elements are a first plurality of cleaning elements and further comprising a second plurality of cleaning elements parallel to the first plurality of cleaning elements and having a cross section similarly shaped to the cross section of the first plurality of cleaning elements, the second plurality of cleaning elements being coupled to the back wall.

16. An apparatus for retracting at least a portion of sides of an animal tongue, at least a portion of a back of the tongue, and a dorsal portion of the animal tongue, comprising:
   a tongue retraction handle that is elongate and comprises a proximal portion that extends along a reference plane toward a distal portion, the tongue retraction handle including at least one reinforcement to resist shape deformation, with the tongue retraction handle generally disposed above a reference plane; and
   means for cupping the tongue coupled to and continuous with the distal portion of the tongue retraction handle, the means for cupping extending along the reference plane generally beneath the reference plane, the means for cupping for retracting the animal tongue laterally,
   wherein the means for cupping the tongue include a tongue retraction cup sized to locate a first side of the tongue retraction cup over a first lateral side of the tongue to forcibly retract the tongue laterally, the tongue retraction cup being sized to locate a second side opposite the first side and over a second side of the tongue that is opposite the first lateral side of the tongue to forcibly retract the tongue laterally, the tongue retraction cup being sized to locate a posterior extending tip at least partially along the back of the tongue toward an oral pharyngeal portion of the tongue to retract the tongue, the first side, second side, and posterior extending tip defining a tongue receiving cavity of the tongue retraction cup, wherein the tongue retraction cup is sized to locate a first side over a first side of the tongue while the second side is disposed over the second side of the tongue, and the dorsal portion of the cup is disposed over the back of the tongue, and wherein the apparatus is formed of one or more materials adapted to maintain a shape, including an orientation of the tongue retraction handle with respect to means for cupping the tongue to forcibly retract the animal tongue laterally.

17. The apparatus of claim 16, wherein the means for cupping the tongue of the animal comprise means for cupping the tongue by cupping an oral portion of the tongue and by at least partially cupping an oral pharyngeal portion of the tongue.

18. The apparatus of claim 16, wherein the apparatus for retracting at least a portion of sides of an animal tongue, at least a portion of a back of the tongue, and a dorsal portion of the animal tongue is for cleaning the animal tongue and further comprising means for cleaning the tongue coupled to the means for cupping the tongue.

19. An apparatus for retracting at least a portion of sides of an animal tongue, at least a portion of a back of the animal tongue, and a dorsal portion of an animal tongue, comprising:
 a tongue retraction handle that is elongate comprising a proximal portion that extends along a reference plane toward a distal portion, with the tongue retraction handle generally disposed above the reference plane; and
 a tongue retraction cup coupled to and continuous with the distal portion of the tongue retraction handle, the tongue retraction cup extending along the reference plane and generally beneath the reference plane, the tongue retraction cup being generally concave and shaped such that a first side of the tongue retraction cup is sized to extend at least partially over a first lateral side of the tongue to forcibly retract the tongue laterally, a second side opposite the first side is sized to extend at least partially over a second side of the tongue that is opposite the first lateral side of the tongue to forcibly retract the tongue laterally, a dorsal portion of the cup is sized to extend along the dorsal portion of the tongue and a posterior extending tip is sized to extend at least partially along the back of the tongue toward an oral pharyngeal portion of the tongue to retract the tongue, the first side, second side, and posterior extending tip defining a tongue receiving cavity of the tongue retraction cup, wherein the tongue retraction cup is sized to locate the first side over the first side of the tongue while the second side is disposed over the second side of the tongue, and the dorsal portion of the cup is disposed over the back of the tongue, and wherein the apparatus is formed of one or more materials adapted to maintain a shape, including an orientation of the tongue retraction handle with respect to the tongue retraction cup, to forcibly retract the animal tongue laterally.

20. The apparatus of claim 19, wherein the apparatus is for cleaning the animal tongue, and further comprising cleaning elements coupled to the tongue retraction cup and extending away from the tongue retraction cup and into the tongue receiving cavity.

21. The apparatus of claim 19, wherein the tongue retraction handle includes at least one reinforcement to resist shape deformation.

* * * * *